United States Patent [19]

McGowan et al.

[11] 4,355,169

[45] Oct. 19, 1982

[54] THIAZOLIDINYL-SUBSTITUTED PHENYL SULFONAMIDES

[75] Inventors: Donald A. McGowan; Frank A. Meneghini, both of Arlington, Mass.

[73] Assignee: Polaroid Corporation, Cambridge, Mass.

[21] Appl. No.: 239,357

[22] Filed: Mar. 2, 1981

[51] Int. Cl.³ .......................................... C07D 277/04
[52] U.S. Cl. .................................... 548/146; 260/158
[58] Field of Search ....................... 548/146, 152, 148; 260/158; 564/84, 89, 86

[56] References Cited

U.S. PATENT DOCUMENTS

| | | | |
|---|---|---|---|
| 2,236,825 | 4/1941 | Mares et al. | 564/84 |
| 2,298,443 | 10/1942 | Weissberger | 564/84 |
| 3,679,657 | 7/1972 | Desai et al. | 548/152 |
| 3,719,489 | 3/1973 | Cieciuch et al. | |
| 4,098,783 | 7/1978 | Cieciuch et al. | |
| 4,153,606 | 5/1979 | Scherberich | 548/146 |
| 4,282,364 | 8/1981 | Amato et al. | 548/146 |

*Primary Examiner*—Thomas A. Waltz
*Assistant Examiner*—Raymond Covington
*Attorney, Agent, or Firm*—Sybil A. Campbell

[57] ABSTRACT

This invention is concerned with certain 3-(thiazolidin-2'-yl)-substituted phenyl sulfonamides which find utility as intermediates in the preparation of photographic image dye-providing materials.

5 Claims, No Drawings

THIAZOLIDINYL-SUBSTITUTED PHENYL SULFONAMIDES

FIELD OF THE INVENTION

This invention relates to certain 3-(thiazolidin-2'-yl)-4-hydroxy-phenyl sulfonamides useful as intermediates in the preparation of photographic image dye-providing materials.

BACKGROUND OF THE INVENTION

U.S. Pat. No. 3,719,489 describes and claims photographic processes employing certain photographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Compounds disclosed as useful in liberating a reagent in the presence of said silver ions and/or silver complex are sulfur-nitrogen compounds containing the group $$-S-X-\overset{|}{N}- \text{ or } -S-X-N=$$

wherein X is

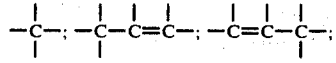

These 1,3-sulfur-nitrogen compounds may be linear or cyclic in structure, and in a particularly preferred embodiment are thiazolidine compounds, such as, compounds which comprise a dye radical having the chromophoric system of an azo, anthraquinone, phthalocyanine or other dye and a thiazolidin-2'-yl moiety which may be bonded directly to the dye radical or through an appropriate linking group.

U.S. Pat. No. 4,098,783, a continuation-in-part of Ser. No. 465,694, now abandoned, which is a division of said U.S. Pat. No. 3,719,489 discloses that dyes substituted with a thiazolidin-2'-yl moiety may be synthesized by condensing a dye possessing an aldehyde group with a 2-aminoethanethiol, or rather than forming the thiazolidin-2'-yl moiety as the final step in the synthesis, an intermediate possessing an aldehyde group may be condensed with the selected 2-aminoethanethiol and the condensation product then reacted with the appropriate molecule or molecules to yield the final dye product. For example, an intermediate comprising a linking group substituted with a thiazolidin-2'-yl moiety may be synthesized from a selected aldehyde in several steps including the condensation with a 2-aminoethanethiol and the linking group then reacted as an amine with a dye radical possessing, e.g., a sulfonyl chloride substituent or it may be reacted as a sulfonyl chloride with a dye radical possessing an amino substituent.

The present invention is concerned with a particular class of thiazolidine-substituted compounds useful as intermediates in the preparation of the aforementioned dyes.

SUMMARY OF THE INVENTION

It is, therefore, the primary object of the present invention to provide certain 3-(thiazolidin-2'-yl)-4-hydroxy-phenyl sulfonamides.

Other objects of the present invention will in part be obvious and will in part appear hereinafter.

The invention accordingly comprises the products and compositions possessing the features, properties and relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

Specifically, the 3-(thiazolidin-2'-yl)-substituted phenyl sulfonamides of the present invention may be represented by the formula

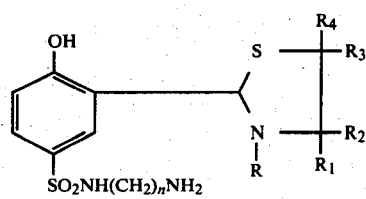

wherein R is selected from alkyl, usually containing 1 to 20 carbon atoms, aryl, e.g., phenyl and aralkyl, e.g., phenyl-substituted alkyl, usually alkyl containing 1 to 20 carbon atoms; $R_1$, $R_2$, $R_3$ and $R_4$ each are selected from hydrogen, alkyl, usually containing 1 to 20 carbon atoms, and phenyl; and n is 2 to 10. The alkyl, aryl and aralkyl groups comprising R, $R_1$, $R_2$, $R_3$ and $R_4$ may be unsubstituted or substituted with a group, such as, carboxy, alkoxy and hydroxy. Preferably, when R is alkyl, it contains at least 10 carbon atoms, i.e., 10 to 20 carbon atoms.

The subject compounds may be synthesized in a conventional manner by reacting a 3-(thiazolidin-2'-yl)-phenyl sulfonyl chloride with an excess of an alkylene diamine, $H_2N(CH_2)_nNH_2$, or by reacting said sulfonyl chloride with a bromoalkylamine hydrobromide, $Br(CH_2)_nNH_2 \cdot HBr$, followed by converting the bromo group of the bromoalkyl sulfonamide to a primary amino group using potassium phthalimide.

Typical sulfonyl chlorides that may be employed are those having the formula

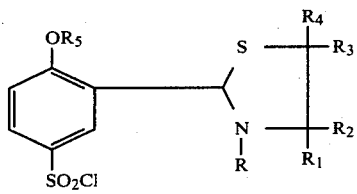

wherein R is selected from alkyl, usually containing 1 to 20 carbon atoms, aryl, e.g., phenyl and aralkyl, e.g., phenyl-substituted alkyl, usually alkyl containing 1 to 20 carbon atoms; $R_1$, $R_2$, $R_3$ and $R_4$ each are selected from hydrogen, alkyl usually containing 1 to 20 carbon atoms, and phenyl; and $R_5$ is hydrogen or acyl, e.g., benzoyl. The alkyl, aryl and aralkyl groups comprising R, $R_1$, $R_2$, $R_3$ and $R_4$ may be unsubstituted or substituted with a group, such as, carboalkoxy, alkoxy, alkenyl and benzoyloxy. Preferably, when R is alkyl, it contains at least 10 carbon atoms, i.e., 10 to 20 carbon atoms. These compounds also may be reacted with the amine reactant as their hydrochloride salts. These sulfonyl chlorides form the subject matter of copending U.S. patent application Ser. No. 239,358 of Myron S. Simon filed concurrently herewith and may be prepared from the corresponding aniline as disclosed therein or may be prepared via direct sulfonation of salicylaldehyde as disclosed and claimed in copending U.S. patent application Ser. No. 239,356 of Charles A. Kelly and Frank A. Meneghini also filed concurrently herewith.

The amine reactants are known compounds that can be synthesized in a conventional manner and many are available commercially.

The following examples are given to further illustrate the present invention and are not intended to limit the scope thereof.

EXAMPLE 1

Preparation of the compound having the formula

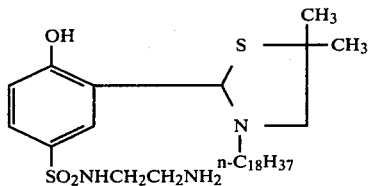

3-(5',5'-dimethyl-N-n-octadecyl-thiazolidin-2'-yl)-4-benzoyloxy-phenyl sulfonyl chloride (0.500 g, 0.75 mmoles) in 5 ml tetrahydrofuran (THF) was added dropwise to a 150 ml 0° C. THF solution of 10 ml ethylenediamine (200 molar excess). After the slow addition was complete, the mixture was allowed to stir at room temperature for two hours. Water (15 ml) was then added and the solution stirred an additional 10 minutes. Additional water and ether was added and the mixture transferred to a separatory funnel. Concentrated HCl was added until the water layer was acidic to litmus. The ether layer was separated, dried over sodium sulfate and evaporated to give very little oily material. The acidic water layer was re-extracted several times with chloroform, the extracts dried and evaporated to give an oil, 420 mg. TLC in 20% methanol/chloroform showed basically one spot. nmr in $CDCl_3$ was very broad but sharpened in N,N-dimethylformamide-$d_5$ and conclusively showed that the benzoyl group had been removed. Also, the integration for the rest of the resonances was in very good agreement for the structure of the title compound.

EXAMPLE 2

The compound of Example 1 also was prepared as follows:

(a) 3-(5',5'-dimethyl-N-n-octadecyl-thiazolidin-2-yl)-4-benzoyloxy-phenyl sulfonyl chloride (21.8 g, 32.8 mmoles) and bromoethylamine hydrobromide (7.40 g, 36.1 mmoles) were mutually combined in the minimum amount of N,N-dimethylformamide (DMF) to give a dark solution. Triethylamine (10 ml, 2 eq.) was then added and the resulting light green solution was allowed to stir for 2 hours at room temperature. Pouring of the DMF solution into dilute HCl followed by chilling gave a gummy precipitate which was difficult to decant from. Instead, a partition with chloroform followed by separation and evaporation gave a more concentrated DMF solution of the product. Precipitation of the product with dilute HCl followed by partitioning between ether and water and washing of the ether layers with water gave 16.2 g (66%) of the product as an oil following drying and evaporation of the ether.

(b) The bromoethyl sulfonamide prepared in step (a) (2.72 g, 3.62 mmoles) and potassium phthalimide (670 mg, 3.62 mmoles) were stirred together in the minimum amount of DMF to give a light yellow solution. The mixture was stirred at 60° C. for three hours at which point the TLC ($CHCl_3$) showed no starting material and one major product spot. After standing overnight, the mixture was poured into dilute HCl and chilled. The supernatant was decanted and the precipitate washed repeatedly with water. It was then taken up in chloroform, dried over sodium sulfate and evaporated to give 1.75 g of gummy solid. This material was dissolved in hexane and chilled (dry ice) to give a gummy precipitate. The supernatant was decanted and the precipitate dried to give purified phthalimido-substituted sulfonamide, 1.15 g.

The foregoing reaction was repeated using 16.2 g of bromoethyl sulfonamide and 3.99 g of potassium phthalimide and heating at 60° C. for 5 hours followed by precipitating and partitioning with ether/water to give 14.5 g of phthalimido-substituted product.

(c) The phthalimido-substituted compound of step (b) (10 g, 12.2 mmoles) was taken up in ethanol (300 ml) and hydrazine hydrate (1.83 g, 3 eq.) added. The mixture was allowed to stir at room temperature for 48 hours and then filtered. The filtrate was heated to boiling for one-half hour and then evaporated in vacuo. TLC showed no starting material in the residue. The residue was taken up in ether, filtered of insolubles and allowed to stand overnight. Fine white crystals were then filtered off and a second, smaller crop obtained on concentration of the filtrate. The filtrate was evaporated to give 5.82 g of yellow oil which was taken up in chloroform, treated with charcoal with warming, filtered through celite and evaporated. The yellow oil remaining tended to solidify upon standing. TLC (10% methanol/chloroform) showed 11 spots, but the major one was a streak from the origin, as expected for the title compound. nmr also suggested the title compound.

EXAMPLE 3

The compound of Example 1 also was prepared from the hydroxy-substituted phenyl sulfonyl chloride as follows.

To 80 ml of dry dichloromethane stirred at −5° to 0° C. was added 9.04 g (150 mmoles) of ethylenediamine. To the solution was added 2.00 g (3.30 mmoles) of 3-(5',5'-dimethyl-N-n-octadecyl-thiazolidin-2'-yl)-4-hydroxy-phenyl sulfonyl chloride.hydrochloride in 10 ml of dichloromethane using an addition funnel. The sulfonyl chloride was added at a rate such that the temperature remained between about 0° and 5° C. The mixture was then stirred at 0° C. for 1.5 hours. It was then extracted with 100 ml (×2) of 1 N HCl, 100 ml of water, and 100 ml of brine. The organic layer was dried over magnesium sulfate. The magnesium sulfate was removed by filtration, and 70 ml of hexane was added to the stirring dichloromethane solution. Dry HCl was slowly bubbled through the solution until no more was absorbed. The solvent was evaporated in vacuo to dryness yielding the dihydrochloride of the title compound as a pale yellow solid: 1.92 g (2.80 mmoles); 85.4% by weight yield.

As noted above, the sulfonamides of the subject invention are useful as intermediates in the synthesis of photographic image dye-providing materials, such as, the thiazolidine-substituted dyes described and claimed in aforementioned U.S. Pat. No. 4,098,783. For this purpose, the subject compounds may be reacted with a dye substituted with, e.g., a —COCl or —SO₂Cl group to give the image dye-providing material. As an illustration, 280 mgs of the compound prepared in Example 1 and 190 mgs (one equivalent) of the yellow dye of the formula

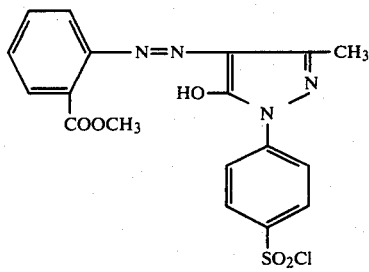

were combined in pyridine and allowed to stir overnight. The pyridine was evaporated, dilute HCl added, and the residue triturated and filtered. The residue was taken up in chloroform, dried over sodium sulfate and concentrated. The solution was applied to a Florosil column (chloroform) and eluted with chloroform and 20% acetone/chloroform to give 210 mgs of the desired image dye-providing material of the formula

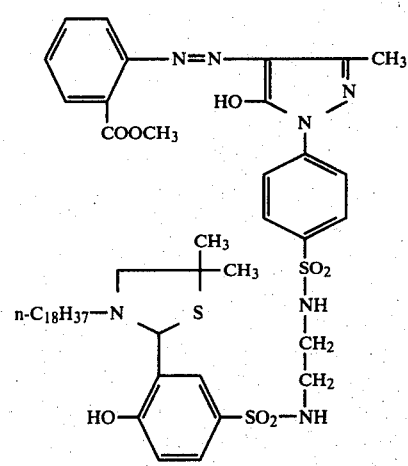

which was confirmed by nmr (CDCl₃).

Examples of other image dye-providing compounds that may be prepared from the subject intermediates are those disclosed in copending U.S. patent application Ser. No. 143,284 of Ruth C. Bilofsky, Ronald F. Cieciuch, Louis Locatell, Jr., Howard G. Rogers and Charles M. Zepp filed Apr. 24, 1980 (now U.S. Pat. No. 4,264,701), which is a continuation-in-part of U.S. Patent application Ser. No. 32,888 filed Apr. 24, 1979, now abandoned.

Since certain changes may be made in the herein described subject matter without departing from the scope of the invention herein involved, it is intended that all matter contained in the above description and examples be interpreted as illustrative and not in a limiting sense.

What is claimed is:

1. A compound of the formula

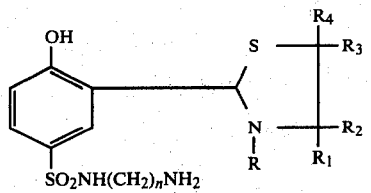

wherein R is selected from alkyl, aryl and aralkyl; $R_1$, $R_2$, $R_3$ and $R_4$ each are selected from hydrogen, alkyl and phenyl; and n is 2 to 10.

2. A compound as defined in claim 1 wherein R is alkyl.

3. A compound as defined in claim 1 wherein $R_3$ and $R_4$ are alkyl.

4. A compound as defined in claim 1 wherein n is 2.

5. The compound

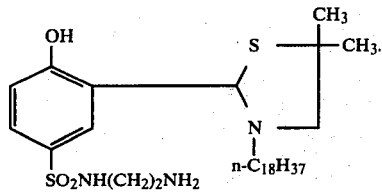

* * * * *